(12) United States Patent
Heintze (10) Patent No.: US 8,994,817 B2
(45) Date of Patent: Mar. 31, 2015

(54) INFRARED INSPECTION OF METALLIC WEB STRUCTURES

(75) Inventor: David P. Heintze, Anderson, SC (US)

(73) Assignees: Michelin Recherche et Technique S.A., Granges-Paccot (CH); Compagnie Generale des Etablissements Michelin, Clermont-Ferrand (FR)

( * ) Notice: Subject to any disclaimer, the term of this patent is extended or adjusted under 35 U.S.C. 154(b) by 516 days.

(21) Appl. No.: 13/295,678

(22) Filed: Nov. 14, 2011

(65) Prior Publication Data
US 2013/0120561 A1  May 16, 2013

(51) Int. Cl.
*H04N 7/18* (2006.01)
*G01N 25/72* (2006.01)

(52) U.S. Cl.
CPC ..................................... *G01N 25/72* (2013.01)
USPC ............ 348/135; 152/251; 152/526; 152/531

(58) Field of Classification Search
CPC .................................... H04N 7/18; B60C 9/22
USPC ............. 348/135, 125, 88; 152/251, 526, 531
See application file for complete search history.

(56) References Cited

U.S. PATENT DOCUMENTS

| | | | | |
|---|---|---|---|---|
| 3,789,226 | A | * | 1/1974 | Green et al. ...................... 378/61 |
| 3,944,831 | A | * | 3/1976 | Heisner et al. ................... 378/61 |
| 4,004,693 | A | * | 1/1977 | Tsuji et al. ...................... 209/538 |
| 4,309,610 | A | | 1/1982 | Hillenmeier |
| 4,996,426 | A | * | 2/1991 | Cielo et al. ...................... 250/330 |
| 5,052,218 | A | * | 10/1991 | Iwama ............................. 73/146 |
| 5,303,756 | A | * | 4/1994 | Hill ............................. 152/154.2 |
| 5,698,064 | A | * | 12/1997 | Fujimoto .................... 156/394.1 |
| 6,268,035 | B1 | * | 7/2001 | Carpenter ..................... 428/64.1 |
| 6,327,333 | B1 | * | 12/2001 | Uchida et al. .................... 378/61 |
| 6,461,035 | B2 | | 10/2002 | Meinlschmidt et al. |
| 6,690,016 | B1 | | 2/2004 | Watkins et al. |
| 7,416,624 | B2 | * | 8/2008 | Stoila et al. ...................... 156/64 |
| 7,513,964 | B2 | | 4/2009 | Ritter et al. |
| 7,591,583 | B2 | | 9/2009 | Foes et al. |
| 7,709,794 | B2 | * | 5/2010 | Zhao et al. ................. 250/338.1 |
| 2006/0042366 | A1 | * | 3/2006 | Carrus et al. .................... 73/146 |

(Continued)

FOREIGN PATENT DOCUMENTS

| | | |
|---|---|---|
| DE | 19547303 | 6/1996 |
| JP | 2006250798 | 9/2006 |
| JP | 03834749 | 10/2006 |

OTHER PUBLICATIONS

Gee et al., Textures from stereo-based IR imaging for industrial tire inspection, Proceedings of SPIE—The International Society for Optical Engineering, v 4052, p. 375-384, 2000.

(Continued)

*Primary Examiner* — Richard Torrente
*Assistant Examiner* — Irfan Habib
(74) *Attorney, Agent, or Firm* — Dority & Manning, P.A.

(57) ABSTRACT

Systems and methods for detecting anomalies in web structures used in the formation of tires are disclosed. A thermal imaging device, such as an infrared camera, can be used to scan a portion of web structure as the web structure leaves a calender. The thermal images can be analyzed for temperature differentials in the web structure. The presence of a temperature differential can signify the presence of an anomaly in the web structure, such as a missing or out of place cable anomaly, an improper edge trim anomaly, or a missing rubber material anomaly.

20 Claims, 6 Drawing Sheets

(56) References Cited

U.S. PATENT DOCUMENTS

| | | |
|---|---|---|
| 2006/0262971 A1* | 11/2006 | Foes et al. .................... 382/141 |
| 2007/0018803 A1* | 1/2007 | Lang ............................. 340/442 |
| 2007/0291896 A1* | 12/2007 | Parham et al. ................. 378/37 |
| 2008/0218742 A1* | 9/2008 | Sakoda et al. ................. 356/73 |
| 2009/0314608 A1* | 12/2009 | Rogers et al. ................ 198/358 |
| 2011/0019903 A1* | 1/2011 | Joly et al. .................... 382/141 |
| 2012/0038357 A1* | 2/2012 | Brandon et al. ............. 324/251 |
| 2013/0099123 A1* | 4/2013 | De Amicis et al. ........ 250/341.6 |

OTHER PUBLICATIONS

Gros, X.E., Detection of delamination in tyres using eddy currents, Proceedings of the Institution of Mechanical Engineers, Part D: Journal of Automobile Engineering, v 211 D1, n 1, p. 79-82, 1997 (Abstract only).

* cited by examiner

INFRARED INSPECTION OF METALLIC WEB STRUCTURES

FIELD OF THE INVENTION

The present invention relates to inspection of web structures having a plurality of metallic cables embedded in a viscoelastic material, and more particularly, to inspection of web structures used in the formation of tires.

BACKGROUND OF THE INVENTION

Web structures can be used in the formation of tires to provide part of the carcass structure of the tire or as other reinforcement of the tire. A web structure typically includes a plurality of metallic cables arranged approximately mutually parallel with one another with a given transverse pitch. The metallic cables are typically embedded in a viscoelastic material, such as a rubber material.

A typical process that is used to manufacture web structures includes depositing a layer of rubber material on both sides of a plurality of metallic cables using a calender formed from two rolls capable of pressing heated rubber sheets against each other. The rubber sheets are heated to a temperature sufficient to allow the rubber sheets to be pressed together and to cover the plurality of metallic cables to form the metallic web structure.

Given the high speeds at which the web structures are formed during the calendering process, anomalies can occur in the web structure as it is being manufactured. For instance, a web structure can include a portion having a missing metallic cable due to failure of the metallic cable to be properly fed into the calender. In addition, a web structure can include an out of place metallic cable, such as a cable that is not sufficiently spaced from neighboring cables. As another example, the rubber material can be missing over a portion of the metallic cables, leaving a portion of the metallic cables of the web structure exposed.

Another anomaly that can occur includes an improper web trim along the side edges of the web structure. For instance, in certain cases it can be desirable to trim the web structure such that a metallic cable is within a predetermined distance from the side edge of the web structure. This allows web structures to be joined together along the side edges during formation of the tire. An anomaly can occur if the web structure is improperly trimmed such that a metallic cable is either too close or too far away from the side edge of the web structure.

Existing techniques are known to examine a web structure for anomalies as the web structure leaves the calender. For instance, one known technique makes use of cameras designed to capture visible light images reflected off of the web structure as it leaves the calender. The visible light images captured by the camera can be analyzed to determine the presence of an anomaly, such as missing rubber material over a portion of the web structure. This technique requires the use of expensive high resolution cameras and requires stringent lighting requirements. Moreover, this technique cannot be typically used to detect an out of place or missing cable anomaly or an improper edge trim anomaly in the web structure.

Another known technique makes use of x-ray and beta particle scanners that examine the web structure as it leaves the calender. These systems require very expensive scanning equipment and can be used to detect anomalies such as a missing or out of place cables and improper edge trims, but are not typically suitable for detecting anomalies such as missing rubber material over a portion of the web structure.

Thus, a need exists for a relatively low cost solution for inspecting a web structure as it leaves the calender. A system and method that can detect anomalies such as missing or out of place metallic cable anomalies, improper edge trim anomalies, and missing rubber material anomalies would be particular useful.

SUMMARY OF THE INVENTION

Aspects and advantages of the invention will be set forth in part in the following description, or may be obvious from the description, or may be learned through practice of the invention.

One exemplary embodiment of the present disclosure is directed to a method for inspecting a web structure for use in the formation of a tire as the web structure exits a calender. The web structure includes a plurality of metallic cables embedded in a rubber material. The method includes scanning a portion of the web structure with a thermal imaging device as the web structure exits the calender; capturing one or more thermal images of the web structure with the thermal imaging device; analyzing the one or more images for the presence of a temperature differential that exceeds a threshold; and detecting an anomaly in the web structure based at least in part on the presence of the temperature differential in the thermal image.

Another exemplary embodiment of the present disclosure is directed to a system for inspecting a web structure for use in the formation of a tire as the web structure exits a calender. The web structure includes a plurality of metallic cables embedded in a rubber material. The system includes a thermal imaging device positioned to scan a portion of the web structure as it leaves the calender. The thermal imaging device is configured to capture one or more thermal images of the web structure. The system further includes an image processing system coupled to the thermal imaging device. The image processing system is configured to analyze the one or more thermal images of the web structure for the presence of a temperature differential exceeding a threshold and to detect an anomaly in the web structure based at least in part on the presence of the temperature differential in the thermal image.

Variations and modifications can be made to these exemplary embodiments of the present disclosure.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

For purposes of describing the invention, reference now will be made in detail to embodiments and/or methods of the invention, one or more examples of which are illustrated in or with the drawings. Each example is provided by way of explanation of the invention, not limitation of the invention. In fact, it will be apparent to those skilled in the art that various modifications and variations can be made in the present invention without departing from the scope or spirit of the invention. For instance, features or steps illustrated or described as part of one embodiment, can be used with another embodiment or steps to yield a still further embodiments or methods. Thus, it is intended that the present invention covers such modifications and variations as come within the scope of the appended claims and their equivalents.

Generally, the present disclosure is directed to a system and method for detecting anomalies in web structures used in the formation of tires. A thermal imaging device, such as an infrared camera, can be used to scan a portion of a web structure as the web structure leaves a calender. As will be discussed in detail below, the web structure is still in a thermodynamic state as the web structure leaves the calender. Anomalies such as missing or out of place cables, improper edge trim, or missing rubber material, can cause temperature differentials to occur in the web structure. The anomalies can be detected by analyzing thermal images of the web structure for temperature differentials. In this manner, the subject matter of the present disclosure provides a system and method for inspecting web structures that requires relatively inexpensive equipment and no additional light sources. Moreover, the systems and methods of the present disclosure can detect a greater number of types of anomalies than existing visible light camera systems and x-ray/beta scanner systems.

Figure 1:
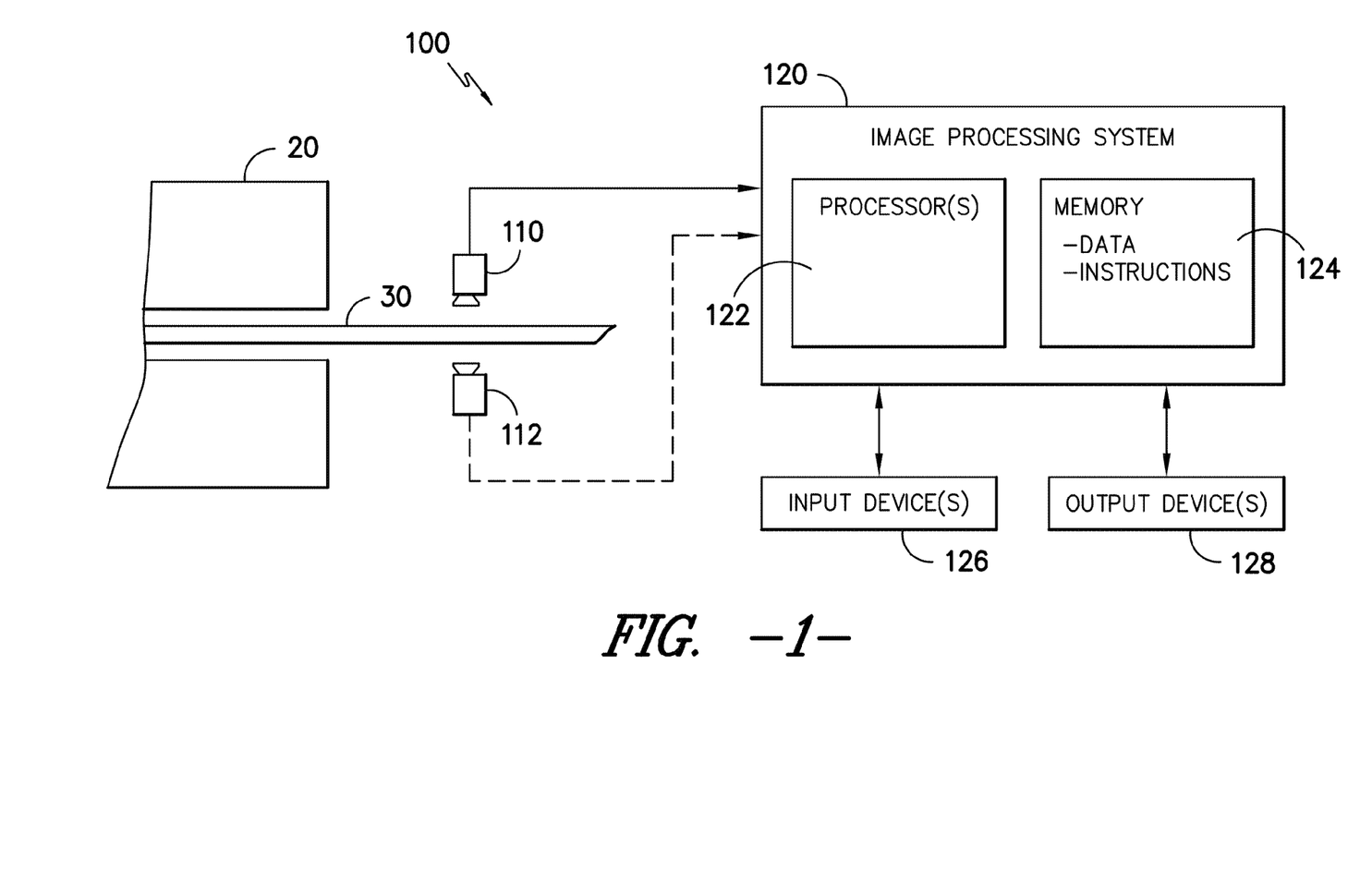
FIG. 1 provides a block diagram of a system for inspecting web structures according to an exemplary aspect of the present disclosure.

FIG. 1 illustrates a schematic overview of an exemplary system 100 for inspecting a web structure 30 as the web structure 30 leaves a calender 20. During the calendering process, a ply of metallic cables is fed into the calender 20 using a cable guide. Layers of viscoelastic material, such as a rubber material, are heated and pressed onto the upper and lower surface of the metallic cables to form the web structure 30.

Figure 2:
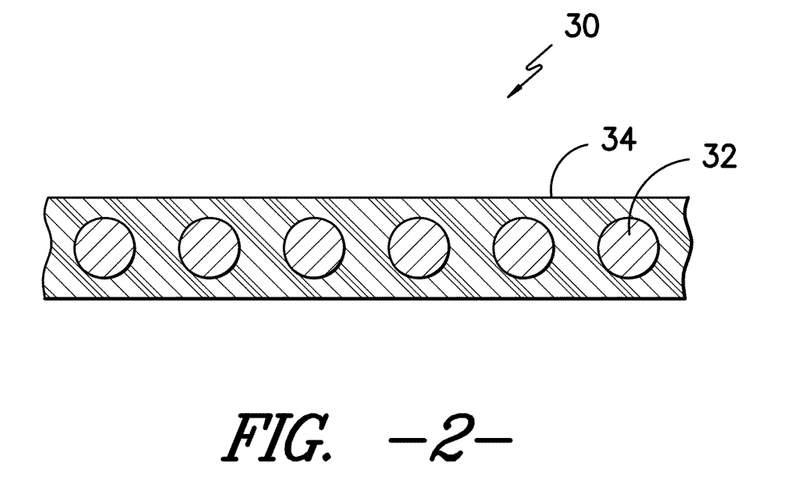
FIG. 2 provides a cross-sectional view of an exemplary web structure according to an exemplary aspect of the present disclosure.

FIG. 2 depicts a cross-sectional view of an exemplary web structure 30. Web structure 30 includes a plurality of metallic cables 32 embedded in a rubber material 34. The plurality of metallic cables 32 are arranged approximately mutually parallel with one another with a given transverse pitch. A layer of rubber material 34 has been pressed onto the top and bottom of metallic cables 32 at an increased temperature and pressure such that the rubber material 34 fills the gaps between the metallic cables 32. While the metallic cables 32 depicted in FIG. 2 are illustrated as solid metallic cables, the metallic cables 32 can also include a plurality of strands or threads arranged according to a predefined configuration with respect to each other. For instance, each of the metallic cables 32 could include between about 2 and about 10 metallic threads of varying diameters.

Once the calendering process is complete, the web structure 30 can be cut and used to form the carcass portion of a tire or to provide other reinforcement for a tire. For instance, the web structure 30 can be used to provide part of the reinforcement at the crown portion of the tire. In certain cases, it can be desirable to trim the web structure 30 such that a metallic cable is within a predetermined distance from the side edge of the web structure 30. This allows web structures to be joined together along the side edges during formation of the tire.

Due to the speed at which the calendering process occurs, anomalies can occur in the web structure 30. For instance, the web structure 30 can include a portion having a missing metallic cable due to failure of the metallic cable to be properly fed into the calender 20. In addition, the web structure 30 can include an out of place metallic cable, such as a cable that is not sufficiently spaced from neighboring cables. As another example, the rubber material can be missing over a portion of the metallic cables, leaving a portion of the metallic cables of the web structure exposed. An anomaly can also occur if the web structure 30 is improperly trimmed such that a metallic cable is either too close or too far away from the side edge of the web structure 30.

Figure 3:
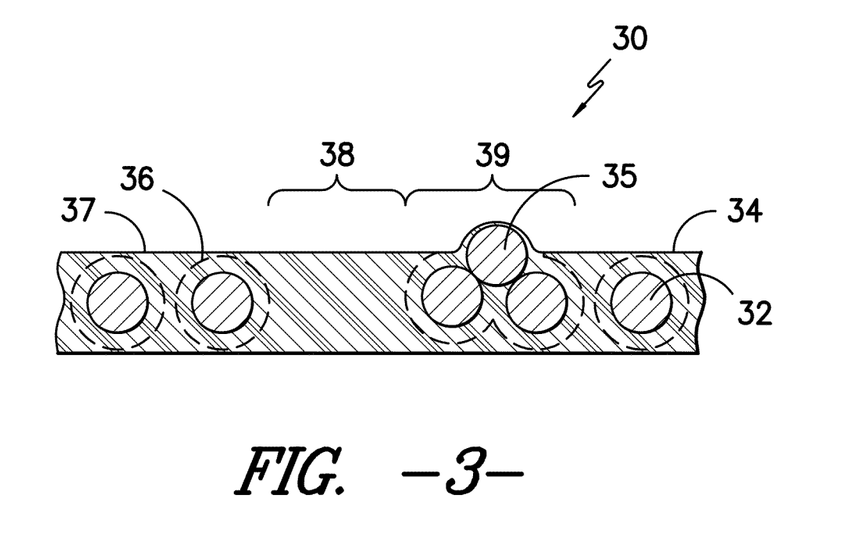
FIG. 3 provides a cross-sectional view of an exemplary web structure comprising an out of place cable anomaly according to an exemplary aspect of the present disclosure.

FIG. 3 provides a cross-sectional view of an exemplary web structure 30 having an out of place cable anomaly. As shown, web structure 30 includes a plurality of cables 32 embedded in a rubber material 34. However, web structure 30 includes a cable 35 that has been improperly placed into web structure 30. In particular, the cable 35 has been improperly located on top of two other cables in the web structure 30. The out of place cable anomaly depicted in FIG. 3 can be detected using the inspection systems and methods according to exemplary aspects of the present disclosure.

As shown in FIG. 1, an exemplary system 100 for detecting an anomaly in the web structure 30 includes a thermal imaging device 110 and an image processing system 120. The thermal imaging device 110 can include an infrared camera configured to capture thermal images of the web structure 30 as it leaves the calender 20. For instance, in a particular embodiment, the thermal imaging device can include infrared camera. The infrared camera can be a low resolution infrared camera (120×120) or a high resolution infrared camera. Those of ordinary skill in the art, using the disclosures provided herein, should understand that any thermal imaging device configured to capture data associated with the thermal properties of the web structure can be used without deviating from the scope of the present disclosure.

The thermal imaging device 110 is positioned to scan a first surface of the web structure 30 as the web structure 30 exits the calender 20. The thermal imaging device 110 captures thermal images of the web structure 30 as the web structure 30 leaves the calender 20. Optionally, the system 100 can include a second thermal imaging device 112 positioned to scan a second surface of the web structure 30 as the web structure 30 exits the calender 20. The thermal imaging device 110 should be positioned to scan the web structure 30 when the web structure 30 is still in a thermodynamic state after leaving the calender 20. For instance, in a particular embodiment, the thermal imaging device 110 is positioned to scan a portion of the web structure 30 within about five seconds or less after the portion of the web structure 30 leaves the calender 20.

Because the thermal imaging device 110 scans the web structure 30 while the web structure 30 is still in a thermodynamic state, the thermal imaging device can be used to detect anomalies in the web structure 30. FIG. 3 depicts a web structure 30 in a thermodynamic state as it leaves the calender 20. As shown, the zone of rubber 36 immediately adjacent to cables 32 is quickly cooled by the cables 32 and is at a decreased temperature relative to the portion of the surface 37 of the web structure 30 that is not immediately cooled by the cables 32.

The presence of metallic cables in the web structure 30 can be readily discerned from thermal images captured by the thermal imaging device 110. For instance, as shown in the thermal image 50 depicted in FIG. 5, the plurality of metallic cables in the web structure 30 is represented by the plurality of vertical dark (or cool) stripes in the web structure 30. The vertical cool stripes in the thermal image are present because the cables cool the rubber material immediately surrounding the cables.

Figure 5:
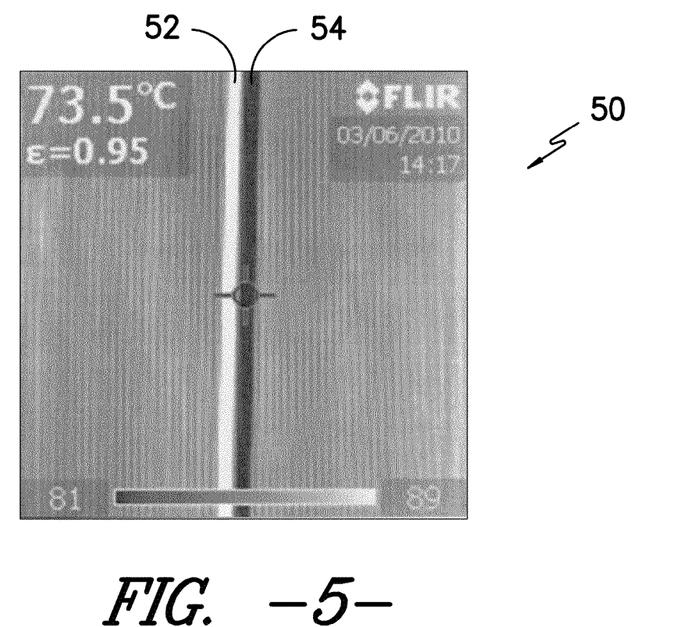
FIGS. 5-9 provide exemplary thermal images depicting various temperature differentials in a web structure according to exemplary aspects of the present disclosure.

Referring back to FIG. 3, the thermal properties of a web structure 30 having an anomaly will be discussed in detail. As shown in FIG. 3, web structure includes a zone 38 where there is a missing cable due to the cable 35 being placed at an improper location in the web structure 30. Because there is no cable in zone 38, the rubber material located in zone 38 will be at an increased temperature relative to the remainder of the web structure 30. This zone of increased temperature 38 is depicted as a hot zone 52 in the exemplary thermal image of FIG. 5. The hot zone 52 of FIG. 5 is a vertical stripe of increased temperature at a location proximate the expected location of the cable.

Referring back to FIG. 3, the presence of an extra cable 35 in zone 39 of the web structure 30 causes the zone 39 to be at a decreased temperature relative to the remainder of the web structure 30. The additional cable 35 located in zone 39 causes the rubber material surrounding the additional cable 35 to be cooled more quickly relative to the remainder of the web structure 30, causing zone 39 to be a zone of decreased temperature. The zone of decreased temperature 39 is depicted as a cool zone 54 in the exemplary thermal image of FIG. 5. The cool zone 54 of FIG. 5 is a vertical stripe of decreased temperature at a location proximate the location of the out of place cable.

Figure 6:
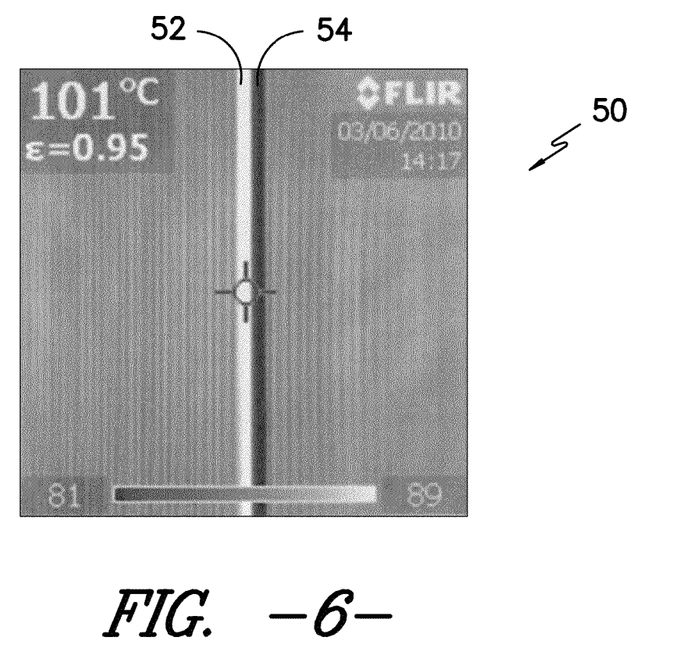

Anomalies in the web structure 30 can be detected by analyzing thermal images captured by the thermal imaging device 110 for temperature differentials that exceed a threshold. For instance, FIGS. 5 and 6 depict a web structure 30 having an out of place cable anomaly. The out of place cable anomaly causes a temperature differential between the hot zone 52 and the cool zone 54 caused by the out of place cable. In particular, as shown in FIG. 5, the temperature of the cool zone 54 is about 73.5° C. As shown in FIG. 6, the temperature of the hot zone 52 is about 101° C. Thus, the out of place cable anomaly has a caused a temperature differential in the web structure of about 27.5° C. This temperature differential can be compared to a threshold, such as a temperature differential threshold of between about 10° C. to about 25° C., to detect an anomaly in the web structure 30.

Figure 7:
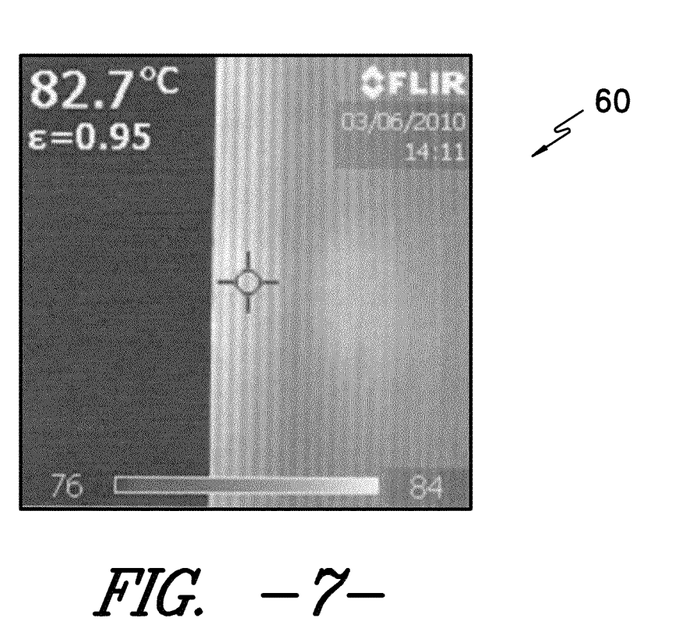
Figure 8:
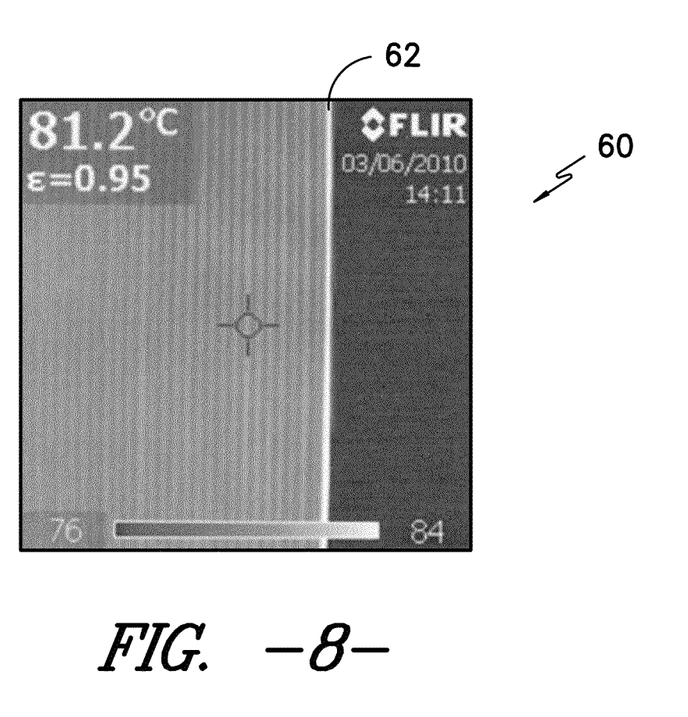

The system 100 can be used to detect other types of anomalies in the web structure, such as an improper edge trim anomaly or a missing rubber material anomaly. FIGS. 7 and 8 provide exemplary thermal images 60 depicting an improper edge trim anomaly in the web structure 30. As shown in the thermal image 60 of FIG. 7, there is no temperature differential or hot zone adjacent the edge of the web structure. The thermal image 70 of FIG. 8, however, includes a hot zone 62 adjacent the edge or side portion of the web structure. This signifies that a metal cable is too far away from the side portion of the web structure, resulting in an increased temperature of the side portion of the web structure. In this regard, an improper edge trim anomaly can be detected by the presence of a temperature differential adjacent the side portion of the web structure.

Figure 9:
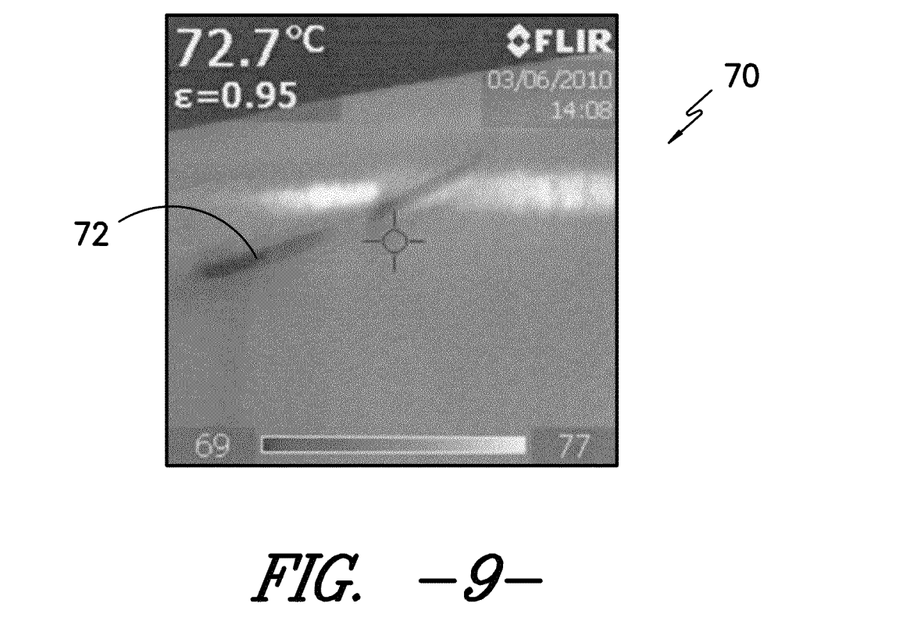

FIG. 9 provides a thermal image 70 depicting a missing rubber material anomaly in the web structure. As shown in the thermal image 70 of FIG. 7, a cool zone 72 is located across the surface of web structure. The cool zone 72 indicates the presence of exposed metal cables in the web structure, signifying the presence of a missing rubber material anomaly. In this regard, a missing rubber material anomaly can be detected by analyzing thermal images for the presence of temperature differential that consists of a cool zone across a surface of the web structure.

Referring back to FIG. 1, the thermal imaging device 110 can be configured to provide thermal images to an image processing system 120. The image processing system 120 can be configured to control the thermal imaging device 110 to capture thermal images of the web structure 30 and can be further configured to analyze the thermal images for temperature differentials to locate anomalies in the web structure 30. For instance, in a particular embodiment, the image processing system 120 can analyze pixel values associated with a plurality of pixels of the thermal image for the presence of a pixel value differential and compare the pixel value differential to a threshold value to detect the presence of an anomaly in the web structure 30.

Image processing system 120 can include one or more processors 122 and memory 124. Processor(s) 122 can be configured to receive input data including infrared images from imaging device 110, to analyze such infrared images with suitable image analysis techniques, and to provide useable output such as data to a user. Memory 124 can include various memory/media elements that may be provided as a single or multiple portions of one or more varieties of computer-readable media, such as, but not limited to, any combination of volatile memory (e.g., random access memory (RAM, such as DRAM, SRAM, etc.) and nonvolatile memory (e.g., ROM, flash, hard drives, magnetic tapes, CD-ROM, DVD-ROM, etc.) or any other memory devices including diskettes, drives, other magnetic-based storage media, optical storage media and others.

The image processing system 120 can be adapted to function as a special-purpose machine providing desired functionality by accessing software instructions rendered in a computer-readable form stored in memory 124. When software is used, any suitable programming, scripting, or other type of language or combinations of languages may be used to implement the teachings contained herein. In other embodiments, the methods disclosed herein may alternatively be implemented by hard-wired logic or other circuitry, including, but not limited to application-specific circuits.

Memory 124 can also include data corresponding to infrared images obtained from the thermal imaging device 110 as well as any predetermined parameters necessary for operation of the inspection system 100. Such predetermined parameters may be pre-programmed into memory 124 or provided for storage therein when entered as input data from a user accessing the input device 126.

Input device 126 may correspond to one or more peripheral or internal devices configured to operate as a user interface with image processing system 120. Exemplary input devices may include but are not limited to a keyboard, touch-screen monitor, touchpad, microphone, mouse, tablet, or other suitable input device.

Image processing system 120 can provide useful data to a user, such as the location of anomalies in a web structure, via an output device 128. Output device 128 may correspond to a display such as a monitor, screen, or other visual display, a printer, or the like. Another specific form of output device may correspond to a process controller. In one embodiment, a process controller can assist the overall web structure manufacturing process by coordinating operating parameters of the calender 20 and thermal imaging device 110.

Figure 4:
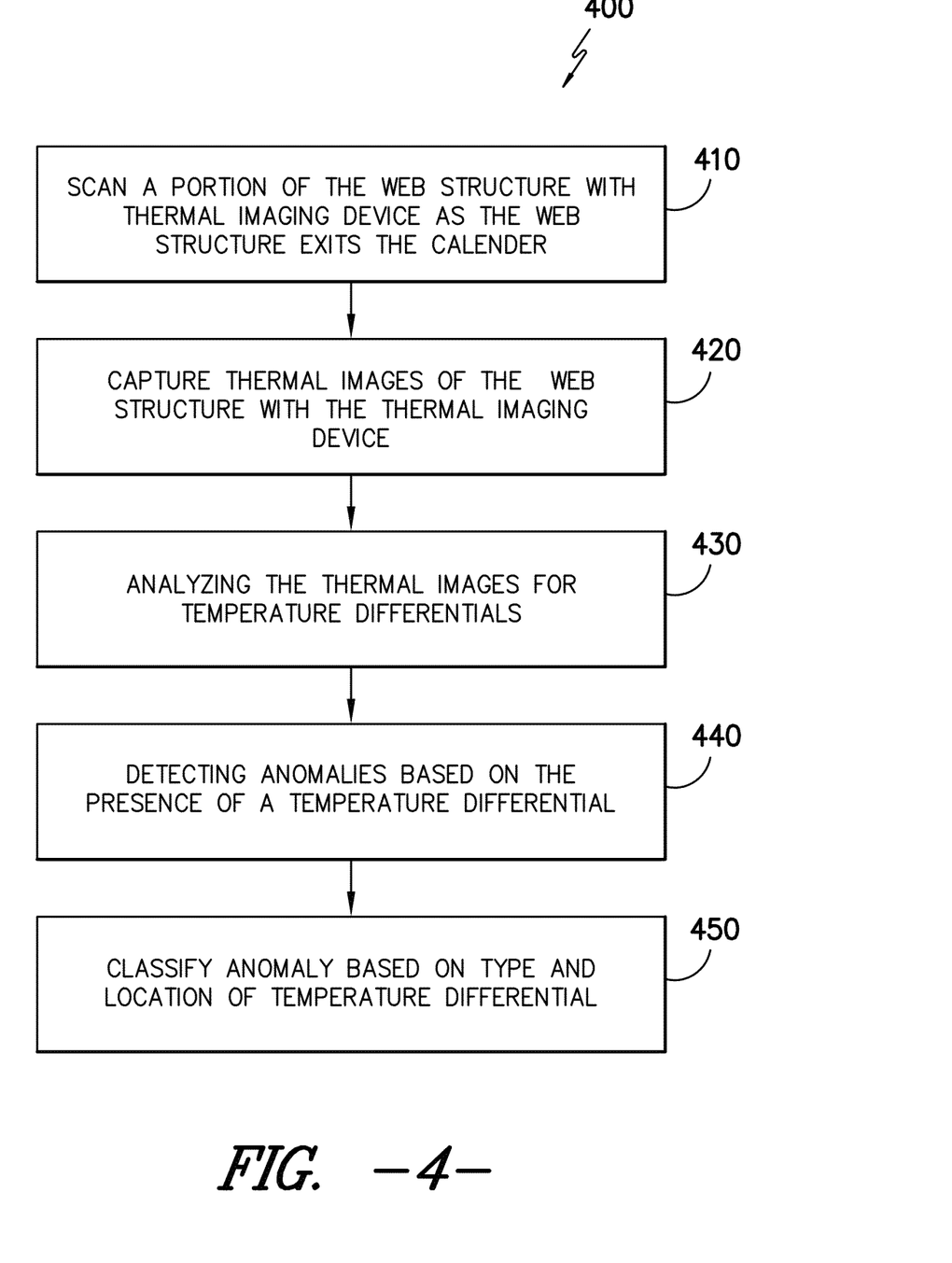
FIG. 4 provides a flow diagram of an exemplary method according to an exemplary aspect of the present disclosure.

FIG. 4 provides a flow diagram of an exemplary method 400 for inspecting web structures as the web structures leave a calender according to an exemplary embodiment of the present disclosure. At 410, the method includes scanning a portion of the web structure with a thermal imaging device as the thermal imaging device leaves the calender. Preferably, the thermal imaging device is positioned to scan the web structure while it is still in a thermodynamic state after leaving the calender. For instance, the thermal imaging device can be positioned to scan the portion of the web structure within about five seconds or less after the web structure leaves the calender.

At 420, the thermal imaging device captures thermal images of the web structure. The thermal images are then analyzed for temperature differentials that exceed a threshold as shown at 430. The presence of a temperature differential exceeding a threshold can signify the presence of an anomaly in the web structure. Accordingly, the method detects anomalies in the web structure based on the presence of a temperature differential in the thermal image as indicated at 440.

At 450, the method includes classifying the anomaly based on the type and location of the temperature differential. In particular, the anomaly can be classified as a missing cable anomaly, an out of place cable anomaly, an improper edge trim anomaly, or a missing rubber material anomaly based at least in part on the type and location of the temperature differential depicted in the thermal image.

For example, the anomaly could be classified as a missing cable anomaly if the temperature differential in the thermal image consists of a hot zone located proximate an expected location of the cable. As discussed with reference to FIG. 3, a missing cable can create a hot zone of rubber due to the absence of a cable to cool the rubber material as it leaves the calender. This hot zone of rubber would appear as striped hot zone at a location proximate the intended location of a cable in a thermal image of the web structure. Accordingly, the presence of a temperature differential that consists of a hot zone proximate the location of an expected cable can signify the presence of a missing cable anomaly.

As another example, the anomaly could be classified as an out of place cable anomaly if the temperature differential in the thermal image comprises a hot zone located proximate the expected location of the cable and a cool zone proximate the hot zone. For instance, FIGS. 5 and 6 depict a thermal image 50 of web structure having an out of place cable anomaly. The out of place cable anomaly causes a temperature differential in the thermal image that comprises a hot zone 52 and a cool zone 54 immediately adjacent the hot zone 52. The presence of the hot zone 52 proximate the expected location of the cable in addition to the presence of the cool zone 54 proximate the location of the hot zone 52 indicates the web structure has an out of place cable anomaly. A thermal image can be analyzed for the presence of a temperature differential comprising a hot zone located proximate a cool zone to detect the presence of an out of place cable anomaly.

As yet another example, the anomaly could be classified as an improper edge trim if the temperature differential comprises a hot zone located proximate a side portion of the web structure. FIG. 8 depicts a thermal image 60 of a web structure having an improper edge trim anomaly. The improper edge trim anomaly results in a hot zone located proximate the side portion of the web structure. Accordingly, a thermal image can be analyzed for the presence of a temperature differential comprising a hot zone adjacent the side portion of a web structure to detect an improper edge trim anomaly in the web structure.

As still another example, the anomaly could be classified as a missing rubber anomaly if the temperature differential consists of a cool zone across the surface of the web structure. FIG. 9 depicts a thermal image 70 of a web structure having a missing rubber anomaly. The missing rubber anomaly results in the presence of a cool zone 72 across the surface of the web structure. Accordingly, the presence of a temperature differential consisting of a cool zone across the surface of the web structure signifies the presence of a missing rubber anomaly in the web structure.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A method for inspecting a web structure for use in the formation of a tire as the web structure exits a calender machine capable of pressing heated rubber sheets against each other, the web structure comprising a plurality of metallic cables embedded in a rubber material, the method comprising:
    scanning a portion of the web structure with a thermal imaging device as the web structure exits the calender machine and the web structure is in a thermodynamic state as a result of the calender machine pressing heated rubber sheets against each other;
    capturing a thermal images of the web structure with the thermal imaging device;
    analyzing the thermal images for the presence of a temperature differential within the thermal image that exceeds a threshold; and
    detecting an anomaly in the web structure based at least in part on the presence of the temperature differential in the thermal image.

2. The method of claim 1, wherein the thermal imaging device comprises an infrared camera.

3. The method of claim 1, wherein the method comprises scanning a portion of the web structure with the thermal imaging device within about five seconds or less after the portion of the web structure exits the calender machine.

4. The method of claim 1, wherein the one or more thermal images are analyzed for the presence of a temperature differential by an image processing system.

5. The method of claim 4, wherein analyzing the one or more thermal images for the presence of a temperature differential by an image processing system comprises:
    analyzing pixel values associated with a plurality of pixels of the thermal image for the presence of a pixel value differential;
    comparing the pixel value differential to a threshold value.

6. The method of claim 1, wherein the method comprises classifying the anomaly based at least in part on the presence of a hot zone or a cool zone in the temperature differential.

7. The method of claim 6, wherein the method comprises classifying the anomaly as a missing cable anomaly if the temperature differential consists of a hot zone at a location on the web structure proximate the expected location of a cable.

8. The method of claim 6, wherein the method comprises classifying the anomaly as an out of place cable anomaly if the temperature differential comprises a hot zone at a location on the web structure proximate the expected location of the cable and a cool zone proximate the hot zone.

9. The method of claim 6, wherein the method comprises classifying the anomaly as an improper edge trim anomaly if the temperature differential comprises a hot zone proximate the edge of the web structure.

10. The method of claim 6, wherein the method comprises classifying the anomaly as a missing rubber material anomaly if the temperature differential consists of a cool zone across the surface of the web structure.

11. A system for inspecting a web structure for use in the formation of a tire as the web structure exits a calender machine capable of pressing heated rubber sheets against each other, the web structure comprising a plurality of metallic cables embedded in a rubber material, the system comprising:
a thermal imaging device positioned to scan a portion of the web structure as it leaves the calender machine and the web structure is in a thermodynamic state as a result of the calender machine pressing heated rubber sheets against each other, the thermal imaging device configured to capture a thermal image of the web structure; and
an image processing system coupled to the thermal imaging device, the image processing system configured to analyze the thermal images of the web structure for the presence of a temperature differential within the thermal image exceeding a threshold and to detect an anomaly in the web structure based at least in part on the presence of the temperature differential in the thermal image.

12. The system of claim 11, wherein the thermal imaging device comprises an infrared camera.

13. The system of claim 11, wherein the system comprises a first thermal imaging device positioned to scan a first surface of the web structure and a second thermal imaging device positioned to scan a second surface of the web structure.

14. The system of claim 11, wherein the thermal imaging device is positioned to scan the web structure within about five seconds or less after the web structure exits the calender machine.

15. The system of claim 11, wherein the image processing system is configured to analyze pixel values associated with a plurality of pixels of the thermal image for the presence of a pixel value differential and to compare the pixel value differential to a threshold value.

16. The system of claim 11, wherein the image processing system is configured to classify the anomaly based at least in part on the presence of a hot zone or a cool zone in the temperature differential.

17. The system of claim 16, wherein the image processing system is configured to classify the anomaly as a missing cable anomaly if the temperature differential consists of a hot zone at a location on the web structure proximate the expected location of a cable.

18. The system of claim 16, wherein the image processing system is configured to classify the anomaly as an out of place cable anomaly if the temperature differential comprises a hot zone at a location on the web structure proximate the expected location of the cable and a cool zone proximate the hot zone.

19. The system of claim 16, wherein the image processing system is configured to classify the anomaly as an improper edge trim anomaly if the temperature differential comprises a hot zone proximate the edge of the web structure.

20. The system of claim 16, wherein the image processing system is configured to classify the anomaly as a missing rubber material anomaly if the temperature differential consists of a cool zone across the surface of the web structure.

* * * * *